United States Patent
Zhu et al.

(10) Patent No.: US 10,463,311 B2
(45) Date of Patent: Nov. 5, 2019

(54) MULTI-CHANNEL BALLISTOCARDIOGRAPHY WITH CEPSTRUM SMOOTHING AND QUALITY-BASED DYNAMIC CHANNEL SELECTION

(71) Applicant: AGENCY FOR SCIENCE, TECHNOLOGY AND RESEARCH, Singapore (SG)

(72) Inventors: Yongwei Zhu, Singapore (SG); Jayachandran Maniyeri, Singapore (SG); Siang Fook Foo, Singapore (SG); Cuntai Guan, Singapore (SG); Hai Hong Zhang, Singapore (SG); Emily Jian Zhong Hao, Singapore (SG); Jiliang Eugene Phua, Singapore (SG); Jit Biswas, Singapore (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 238 days.

(21) Appl. No.: 15/525,043

(22) PCT Filed: Nov. 5, 2015

(86) PCT No.: PCT/SG2015/050436
§ 371 (c)(1),
(2) Date: May 5, 2017

(87) PCT Pub. No.: WO2016/072940
PCT Pub. Date: May 12, 2016

(65) Prior Publication Data
US 2018/0279961 A1    Oct. 4, 2018

(30) Foreign Application Priority Data

Nov. 5, 2014   (SG) .......................... 10201407248W

(51) Int. Cl.
*A61B 5/00* (2006.01)
*A61B 5/11* (2006.01)
(Continued)

(52) U.S. Cl.
CPC ............ *A61B 5/7257* (2013.01); *A61B 5/024* (2013.01); *A61B 5/1102* (2013.01); *A61B 5/113* (2013.01);
(Continued)

(58) Field of Classification Search
CPC ..... A61B 5/7257; A61B 5/024; A61B 5/1102; A61B 5/113; A61B 5/6892; A61B 5/7225;
(Continued)

(56) References Cited

U.S. PATENT DOCUMENTS

2010/0249628 A1  9/2010  Kortelainen
2014/0161280 A1  6/2014  Nackvi

FOREIGN PATENT DOCUMENTS

EP           2063592 A2     5/2009
WO   WO 2007/091199 A2    8/2007
WO   WO 2013/128364 A1    9/2013

OTHER PUBLICATIONS

Yongwei Zhu, et al., "Heart Rate Estimation from FBG Sensors using Cepstrum Analysis and Sensor Fusion", Engineering in Medicine and Biology Society (EMBC), 2014 36th Annual International Conference of the IEEE, pp. 5365-5368 (Aug. 26, 2014).
(Continued)

*Primary Examiner* — Lindsey G Wehrheim
(74) *Attorney, Agent, or Firm* — Womble Bond Dickinson (US) LLP

(57) ABSTRACT

A method for ballistocardiography (BCG) and a BCG system ballistocardiography (BCG) system for heart beat determination are provided. The method includes digitizing a
(Continued)

plurality of signals received from a corresponding plurality of sensors, estimating a plurality of smoothed cepstra corresponding to each of the plurality of digitized signals in response to a smoothed cepstrum analysis of a digital signal at a reception time of each of the plurality of digitized signals, and estimating a fused cepstrum for the plurality of digitized signals in response to the plurality of smoothed cepstra. The method further includes determining a heart rate in response to the plurality of smoothed cepstra and the fused cepstrum.

24 Claims, 10 Drawing Sheets

(51) Int. Cl.
    *A61B 5/024*     (2006.01)
    *A61B 5/113*     (2006.01)
    *G06K 9/00*     (2006.01)

(52) U.S. Cl.
    CPC .......... *A61B 5/6892* (2013.01); *A61B 5/7225* (2013.01); *G06K 9/0053* (2013.01); *A61B 5/7253* (2013.01); *A61B 2562/0266* (2013.01); *A61B 2562/04* (2013.01)

(58) Field of Classification Search
    CPC .......... A61B 5/7253; A61B 2562/0266; A61B 2562/04; G06K 9/0053
    See application file for complete search history.

(56) References Cited

OTHER PUBLICATIONS

Christoph Brüser, et al., "Improvement of Force-Sensor-Based Heart Rate Estimation Using Multichannel Data Fusion", IEEE Journal of Biomedical and Health Informatics, vol. 19(1), pp. 227-235 (Mar. 13, 2014).
PCT International Search Report, 4 pgs. (dated Dec. 14, 2015).
PCT Written Opinion of the International Searching Authority, 5 pgs. (dated Dec. 14, 2015).

| Subject | 1 | 2 | 3 | 4 | 5 | 6 | 7 | 8 | 9 | 10 | 11 | 12 |
|---|---|---|---|---|---|---|---|---|---|---|---|---|
| HR Error Mean | 0.49 | 0.35 | 0.33 | 0.30 | 0.18 | 0.35 | 0.50 | 0.45 | 0.36 | 0.23 | 0.33 | 0.27 |
| HR Error Standard Deviation | 0.51 | 0.52 | 0.56 | 0.32 | 0.27 | 0.34 | 0.46 | 0.54 | 0.43 | 0.42 | 0.39 | 0.37 |

| Subject | 1 | 2 | 3 | 4 | 5 | 6 | 7 | 8 | 9 | 10 | 11 | 12 |
|---|---|---|---|---|---|---|---|---|---|---|---|---|
| Acceptance Rate | 0.93 | 0.95 | 0.94 | 0.90 | 0.97 | 0.95 | 0.85 | 0.88 | 0.96 | 0.99 | 0.95 | 0.93 |

MULTI-CHANNEL BALLISTOCARDIOGRAPHY WITH CEPSTRUM SMOOTHING AND QUALITY-BASED DYNAMIC CHANNEL SELECTION

CROSS-REFERENCE TO RELATED APPLICATIONS

This application is a U.S. National Phase application under 35 USC § 371 of international Application of International Application No. PCT/SG2015/050436, filed Nov. 5, 2015, which claims priority from Singapore Patent Application No. 10201407248W filed on Nov. 5, 2014.

TECHNICAL FIELD

The present invention generally relates to methods and systems for hallistocardiography, and more particularly relates to a method and a system for multi-channel ballistocardiography with cepstrum smoothing and quality-based dynamic channel selection.

BACKGROUND OF THE DISCLOSURE

Ballistocardiography (BCG) is getting increasingly prevalent in medical and healthcare service and products primarily due to the advantage of non-invasivencss. Using various types of pressure sensing devices, the body movement of a subject due to his/her cardio activities are captured and converted to digital signals. Then the heart rates or inter-beat intervals can be estimated from the digital signals for monitoring or diagnostic purposes.

However BCG, in contrast to electrocardiography (ECG), is extremely vulnerable to noise or artefacts in the digital signals since the contact of the sensor as well as the body movement of the subject are uncontrolled. Given that the quality of BCG signals is unknown, the key challenge in BCG analysis is to estimate heart beat events with high reliability and sensitivity.

Multi-channel BCG digital signals captured with an array of sensors contains redundant information on cardio activity of a subject and, in theory, can provide more reliable grounds for heart beat event estimation. Existing methods for BCG digital signal analysis tend to use a signal summing or a signal averaging approach for the fusion of multiple channels.

Cepstrum-based methods for signal periodicity estimation are quite established for audio or speech signal analysis, such as for pitch detection. There are also techniques that are proposed to estimate heart beat intervals from cardio signals, such as BCG. However, as heart beats signals are nonstationary, unlike audio signals, heavy constraints have had to be put in those methods when the cepstrum of the signal is computed. One typical constraint is that the duration of the signal window should cover exactly two heart beats, which would require that the heart rate is initially estimated before the cepstrum of the signal can be computed.

Thus, what is needed is a method and system for improved ballistocardiography with a quick and robust signal analysis technique for estimating heart beat rate with high reliability and sensitivity. Furthermore, other desirable features and characteristics will become apparent from the subsequent detailed description and the appended claims, taken in conjunction with the accompanying drawings and this background of the disclosure.

SUMMARY

According to at least one embodiment of the present invention a method for ballistocardiography is provided. The method includes digitizing a plurality of signals received from a corresponding plurality of sensors, estimating a plurality of smoothed cepstra corresponding to each of the plurality of digitized signals in response to a smoothed cepstrum analysis of a digital signal magnitude at a reception time of each of the plurality of digitized signals, and estimating a fused cepstrum for the plurality of digitized signals in response to the plurality of smoothed cepstra. The method further includes determining a heart rate in response to the plurality of smoothed cepstra and the fused cepstrum.

In accordance with another aspect of the present invention, a ballistocardiography (BCG) system for heart beat determination is provided. The BCG system includes a plurality of BCG sensors, a BCG analyzer and a plurality of communication channels coupled to each of the plurality of BCG sensors and the BCG analyzer. The plurality of BCG sensors generate a corresponding plurality of BCG signals in response to a subject's movement at a location of each of the plurality of BCG sensors and the plurality of communication channels provide the plurality of BCG signals from each of the plurality of BCG sensors to the BCG analyzer. The BCG analyzer is configured to determine a heart rate of the subject in response to a plurality of smoothed cepstra and a fused cepstrum by digitizing the plurality of BCG signals and estimating the plurality of smoothed cepstra corresponding to each of the plurality of digitized BCG signals in response to a smoothed cepstrum analysis of a digital signal magnitude at a reception time of each of the plurality of digitized BCG signals and estimate a fused cepstrum for the plurality of digitized BCG signals in response to the plurality of smoothed cepstra.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with a present invention, by way of non-limiting example only, wherein:

FIG. 9 depicts a table of experimental results heart rate estimation mean determined in accordance with the present embodiment, the table showing mean and standard deviation of the error of the heart rate estimations.

FIG. 10 depicts a table of the experimental results of FIG. 9 showing an acceptance rate in accordance with the present embodiment.

Figure 1:
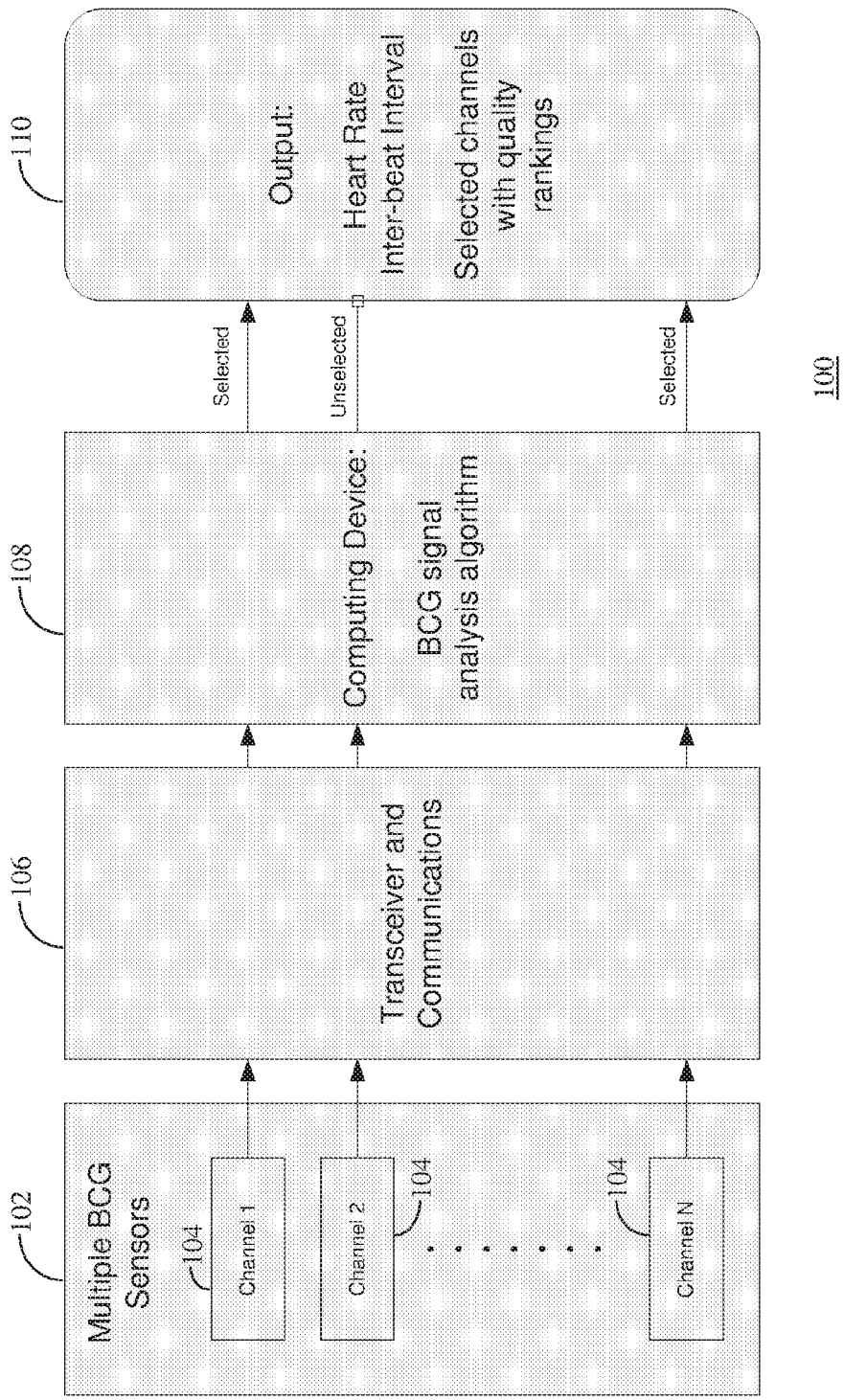
FIG. 1 depicts a block diagram illustrating a multi-channel ballistocardiography (BCG) analysis system in accordance with a present embodiment.

Skilled artisans will appreciate that elements in the figures are illustrated for simplicity and clarity and have not necessarily been depicted to scale. For example, the size of the elements of the BCG system depicted in the block diagram of FIG. 1 are not accurate and are only shown in a manner to help to improve understanding of the BCG system in accordance with the present embodiment.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of this invention to present a method and system which uses a ballistocardiography (BCG) analyzer for analyzing the BCG of human subjects to monitor heart rate and for other applications. The method in accordance with a present embodiment can estimate the heart rate from a short time window of a BCG signal such that the estimation is very close to a heart rate inter-beat interval.

In accordance with the present embodiment, multi-channel BCG is provided simultaneously from multiple sensors, such as a set of fiber optic sensors or other seismic sensors. Microbending sensors and fiber Bragg grating (FBG) sensors are examples of fiber optic sensors utilizable for generating BCG signals in accordance with the present embodiment. The sensors are typically embedded on a supporting material (e.g. a bed mattress) with various spatial layouts. The sensors or a subset of the sensors generate the BCG signals of a human subject when the subject is resting on the supporting material in response to the subject's micro-movements such as heart beats and breathing inhalation and exhalation.

The qualities of BCG signals from different channels are naturally of different qualities due to various conditions present at the time the sensors generate the BCG signals, such as posture and contact conditions. The method in accordance with the present embodiment automatically selects the channels with better quality based on the characteristics of the cepstrum of the BCG signals.

Referring to FIG. 1, a block diagram 100 depicts a setup of a system in accordance with the present embodiment. Multiple BCG sensors 102 generate a corresponding plurality of BCG signals which are provided on a plurality of channels 104 across transceiver and communication circuitry 106 to a computing device 108. The computing device 108 includes a BCG analyzer which performs the processing in accordance with the present embodiment and generates outputs 110 which may include a heart rate based on a calculated inter-beat interval and channel qualities including a dynamically selected monitoring channel.

Figure 2:
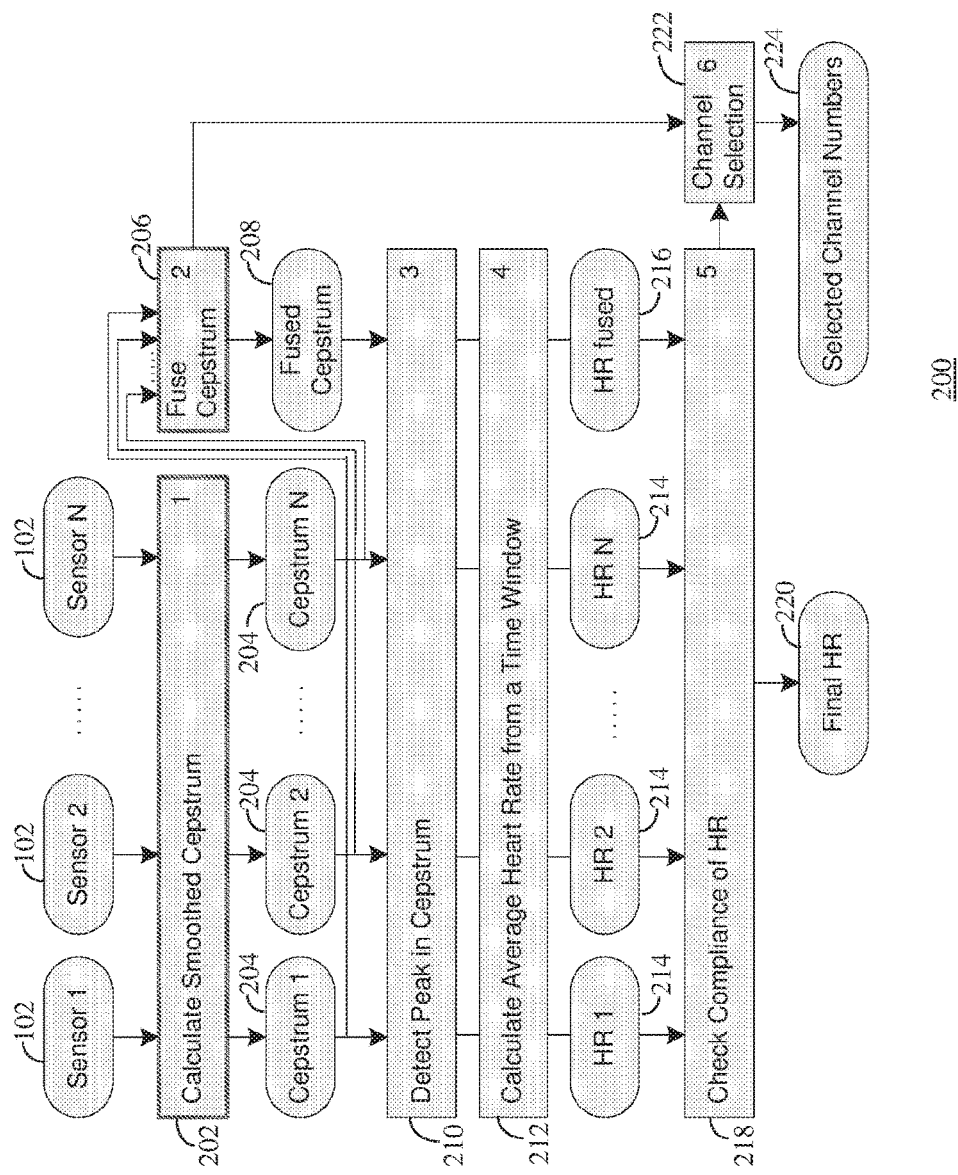
FIG. 2 depicts a flow diagram a BCG analysis method in accordance with the present embodiment.

A flow chart 200 of FIG. 2 depicts the BCG method in accordance with the present embodiment that is performed by the BCG analyzer of the computing device 108. The BCG signals from all the sensors 102 are digitized and provided to a smoothed cepstrum estimator 202 in a digitized form and with a sampling rate and value precision. The smoothed cepstrum estimator 202 performs a smoothed cepstrum analysis of a short time window (e.g., three seconds) sample of digital signal magnitudes at reception times for each of the plurality of digitized BCG signals. The processing is the same for each channel/sensor 102 and the window is shifted with small steps (e.g., one hundred milliseconds) to define a plurality of time shifted predefined time windows to obtain a plurality of time domain samples. At each step, the processing is repeated.

Bandpass filters could also be applied to the windowed signal, such that heart beat related information is passed (i.e., preserved) and certain unrelated movements such as low frequency respiratory information is rejected (i.e., filtered out). Then, smoothed cepstrum estimator 202 calculates a smoothed cepstrum of the plurality of time domain samples of each of the BCG signals using the steps of the flowchart 300 of FIG. 3. A cepstrum is a method typically used for speech analysis based on a cepstral representation of a signal. Calculation of a cepstrum can take the form of obtaining a power spectrum from a logarithm of a power spectrum. In this embodiment, the introduction of a frequency domain windowing function to the cepstrum calculation boils down to applying a low pass filter to the cepstrum, interpreted as a signal, which lets only the slow fluctuations (low frequency oscillations of the curve) pass, hence the smoothing.

Figure 3:
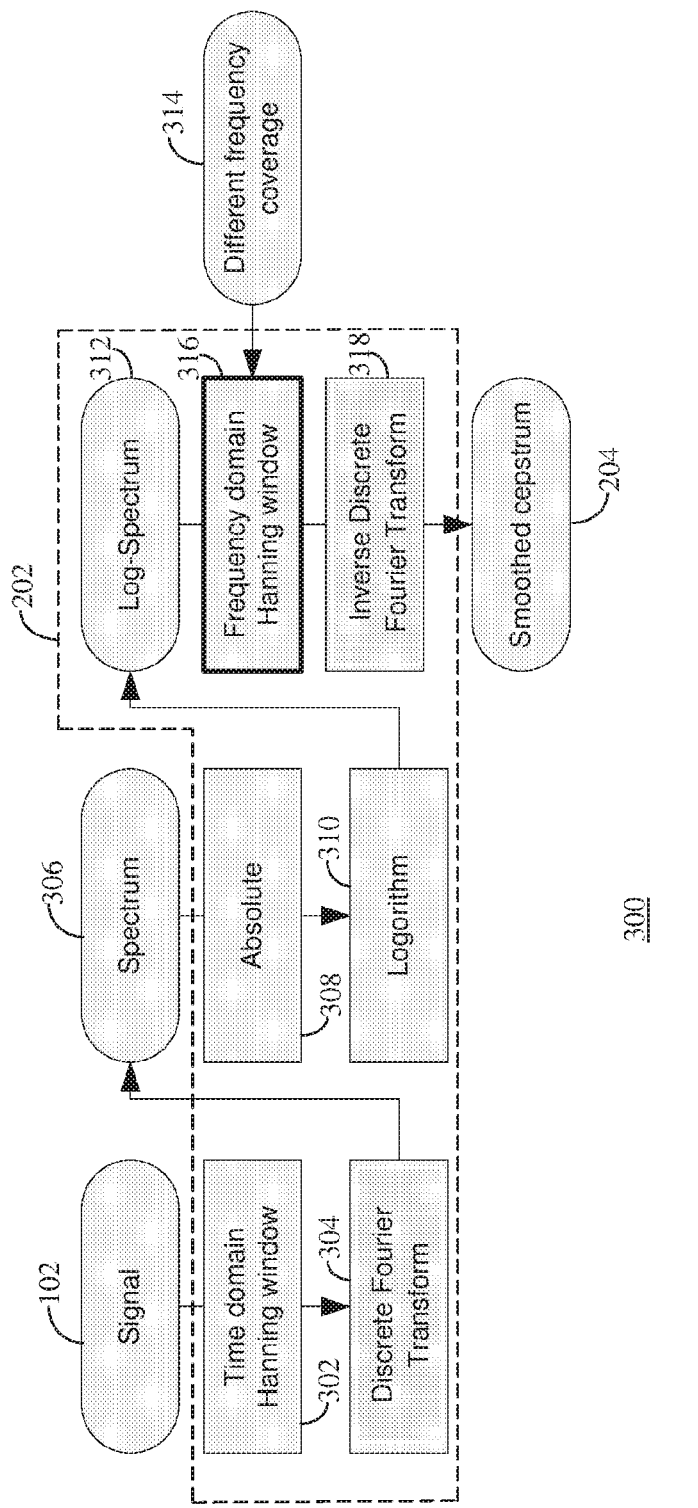
FIG. 3 depicts a flow diagram of calculating a smoothed cepstrum in accordance with the present embodiment.

Thus, referring to FIG. 3, each BCG signal 102 is separated into the plurality of time domain samples in accordance with a time domain Hanning window process 302 and a discrete Fourier transform 304 is performed on the plurality of time domain samples to obtain a spectrum 306 corresponding to the time domain samples of the digitized signal. The absolute values 308 (i.e., the power spectrum) is transformed by a logarithm function 310 to obtain a logarithm power spectrum signal. Then, in accordance with the present embodiment, different defined frequency windows 314 are provided to calculate frequency domain Hanning windows 316 for processing in accordance therewith. The calculated frequency window 316 is applied to the logarithm power spectrum 312, which is then transformed by inverse Fourier transform 318 to estimate the smoothed cepstrum corresponding to the digitized signal. It is noted that the process of the flow chart 300 would be identical to ordinary cepstrum calculations except for the Frequency domain Hanning window step 316.

Window functions are functions that go sufficiently rapidly toward zero. A Hanning window is a raised cosine window is defined in accordance with Equation (1):

$$w(n) = 0.5\left(1 - \cos\left(\frac{2\pi n}{N-1}\right)\right) \tag{1}$$

wherein the ends of the cosine window just touch zero and the side lobes roll off at about 18 dB per octave. The frequency domain Hanning window 316 is applied in accordance with the present embodiment to the log-spectrum 312 such that the smoothed cepstrum 320 is derived with focus on a certain frequency range 314 and appears more smoothed. It is noted that the Frequency domain windowing function is not restricted to a Hanning window function as any other windowing functions with higher weights in the center could be used in accordance with the present embodiment.

Figure 4:
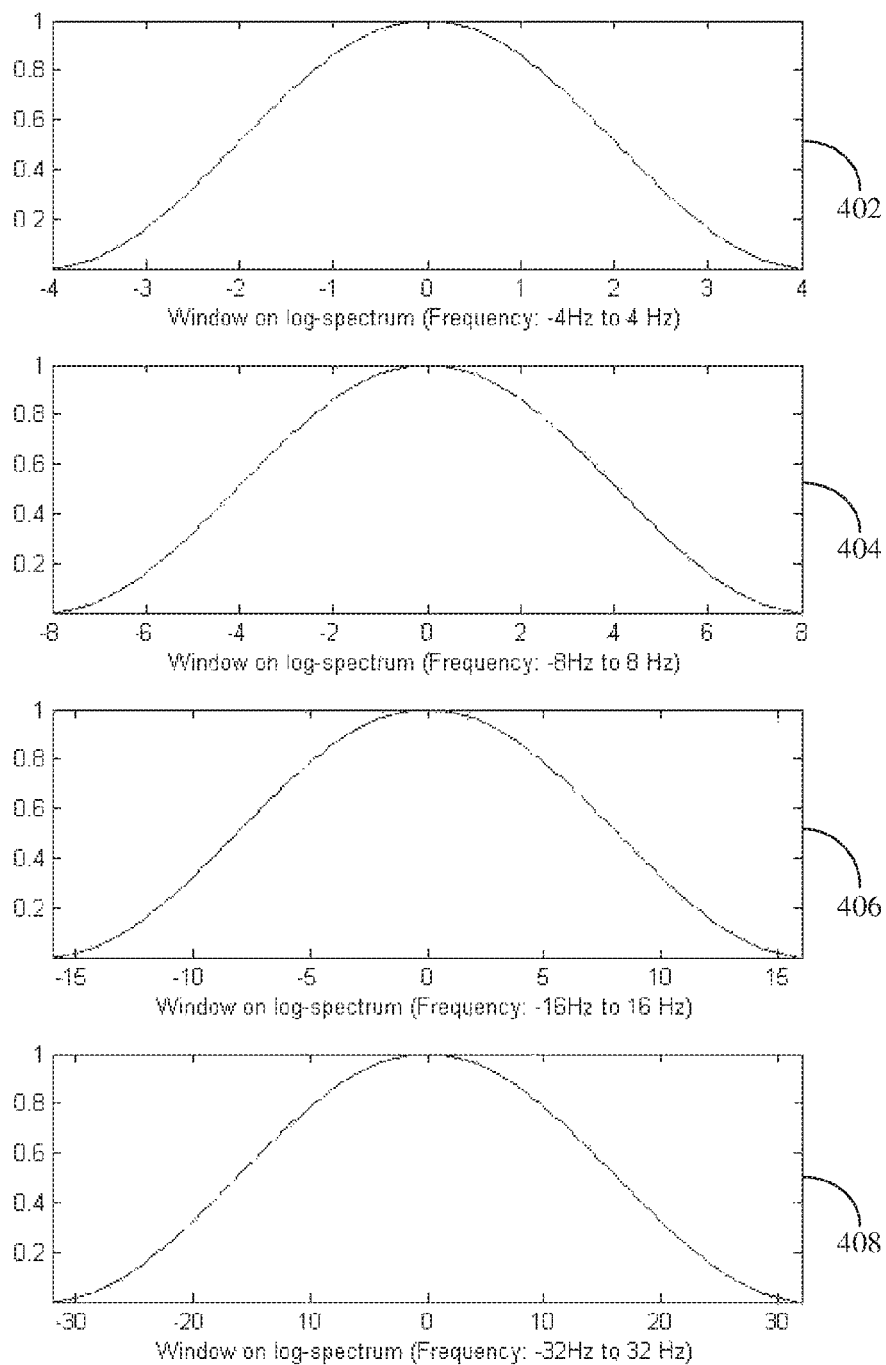
FIG. 4 depicts graphs of frequency domain Hanning windows with various frequency ranges in accordance with the present embodiment.

Referring to FIG. 4, graphs of frequency domain Hanning windows with various frequency ranges are depicted in accordance with the present embodiment. A graph 402 illustrates a frequency domain Hanning window of the frequency range −4 to +4 Hz, a graph 404 illustrates a frequency domain Hanning window of the frequency range −8 to +8 Hz, a graph 406 illustrates a frequency domain Hanning window of the frequency range −16 to +16 Hz and a graph 408 illustrates a frequency domain Hanning window of the frequency range −32 to +32 Hz. The negative frequencies in the Hanning window function correspond to the mirrored log-spectral component above the Nyquist frequency.

Figure 5:
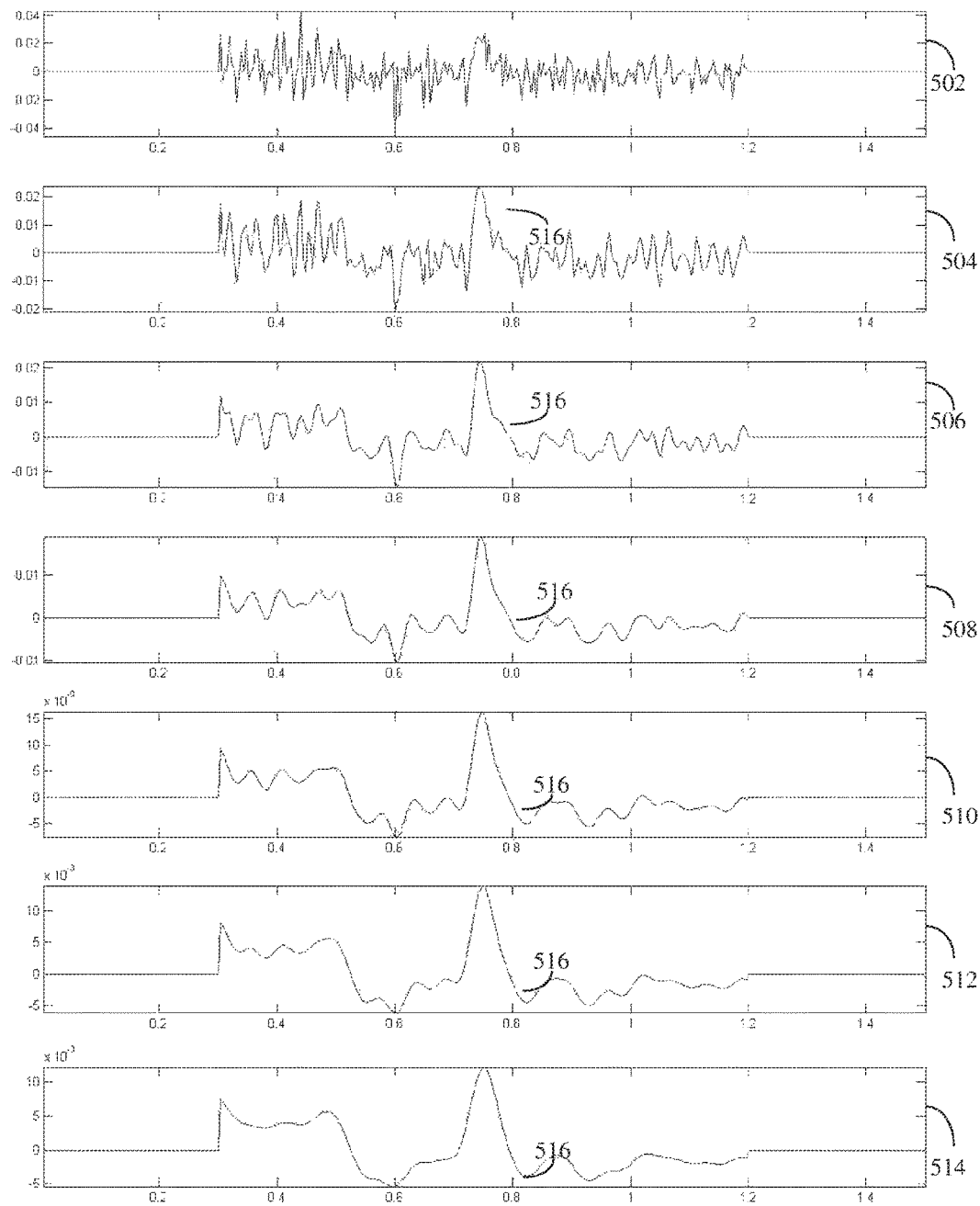
FIG. 5 depicts plots of the effect of smoothed cepstrum by using frequency domain Hanning windows in accordance with the present embodiment.

The effect of applying the frequency domain Hanning window 316 in the cepstrum calculation in accordance with the present embodiment is illustrated in the plots of FIG. 5. A plot 502 shows the cepstrum derived without applying the frequency domain Hanning window step 316. A plot 504 shows the cepstrum derived by applying the frequency domain Hanning window 316 defined 314 to have a frequency range −128 to +128 Hz. A plot 506 shows the cepstrum derived by applying the frequency domain Hanning window 316 defined 314 to have a frequency range −64 to +64 Hz. A plot 508 shows the cepstrum derived by applying the frequency domain Hanning window 316 defined 314 to have a frequency range −32 to +32 Hz. A plot 510 shows the cepstrum derived by applying the frequency domain Hanning window 316 defined 314 to have a frequency range −16 to +16 Hz. A plot 512 shows the cepstrum derived by applying the frequency domain Hanning window 316 defined 314 to have a frequency range −8 to +8 Hz. And a plot 514 shows the cepstrum derived by applying the frequency domain Hanning window 316 defined 314 to have a frequency range −4 to +4 Hz.

It can be observed that a peak 516 at a lag time around 0.75 second advantageously becomes prominent when the frequency domain Hanning window 316 is applied, especially when the frequency range is within −64 to 64 Hz or narrower. The peak 516 is a cepstral peak which has a magnitude corresponding to a cepstral energy value. The peak 516 corresponds to a heart beat interval of 0.75 second.

The frequency ranges of the frequency domain Hanning window 316 can be of other values. However, if the frequency range is too narrow, the interested cepstral peak may also be smoothed out. For heart rate estimation, a frequency domain Hanning window 316 of a frequency range of −32 to +32 is suitable.

Referring back to FIG. 2, at a step 206 estimated cepstrum 204 from multiple channels are fused into one cesptrum, called the fused cepstrum 208. The step 206 of estimating the fused cepstrum comprises selecting a highest value of each of the plurality of smoothed cepstra at each reception time (i.e., each lag time index) of the plurality of digitized signals.

Figure 6:
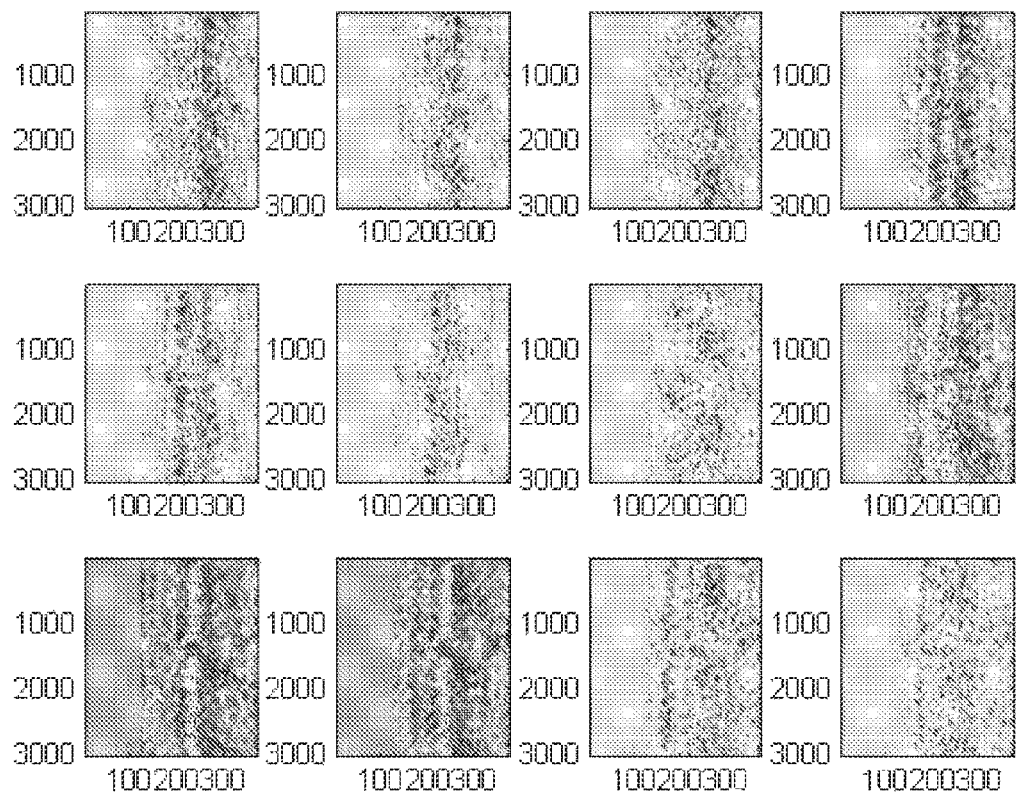
FIG. 6 depicts cepstrograms of the twelve channels of a 12-channel BCG analysis system in accordance with the present embodiment.
Figure 7:
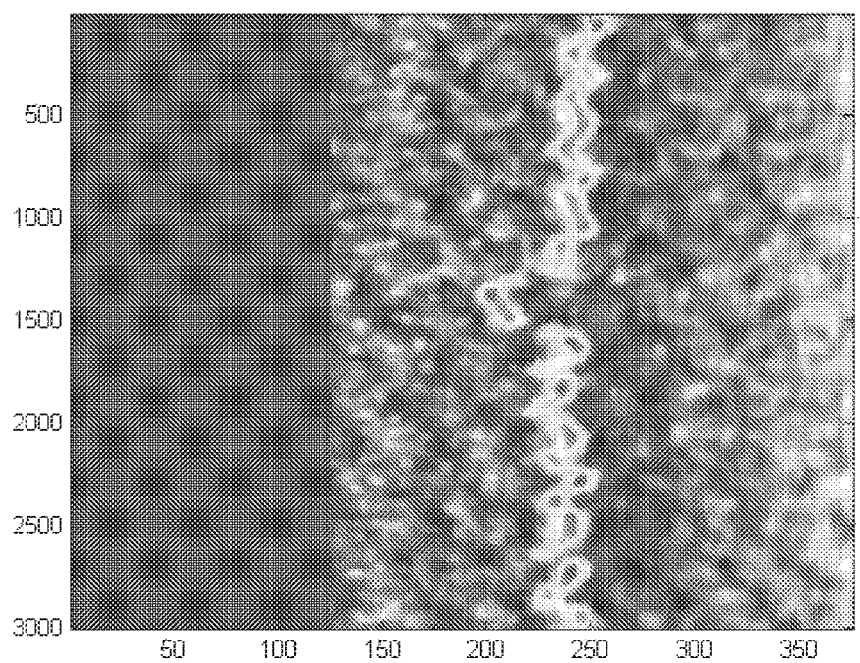
FIG. 7 depicts a cepstogram of a fused cepstrum derived from the cepstrograms of FIG. 6 in accordance with the present embodiment.

Referring to FIG. 6, an illustration 600 depicts cepstrograms of twelve individual channels, and an illustration 700 (FIG. 7) depicts the fused cepstrogram. In general, the fused cepstrum would provide better indication of a heart beat interval than any individual channel.

Referring back to FIG. 2, a cepstral peak is detected 210 within each of the plurality of cepstra 204 and the fused cepstrum 208 in an interested lag time range, if the peak is reaches a predetermined maximal value (i.e., a maximal cepstral energy value) during the lag time range. The lag time range is typically specified by the heart rate range of human being and the cepstral peak is defined by the lag time index and the cepstral energy value. The peak detection 210 is performed in all the channels as well as the fused cepstrum 208.

For heart rate estimation, a longer time window (say fifteen seconds) is used to calculate within the time window 212 an average heart rate 214. The cepstral peaks are checked for continuity within the time window. If the percentage of cepstrum with continuous peaks is above a predetermined threshold, the average heart rate 214 is derived by the mean lag time between the peaks. Thus, the average heart rate 214 can be calculated by Equation (2):

$$HR = 60/T\_lag \quad (2)$$

where T_lag is the mean lag time of the cepstral peaks. If the percentage is below the predetermined threshold, the average heart rate 214 for the time window is not estimated (i.e., is set to null).

The heart rate 216 estimated from the fused cepstrum 208 is checked for compliance with the heart rate 214 estimated from each of the individual channels. Compliance is based on the closeness of the estimated heart rates. The final heart rate 220 is declared if the number of compliant channels is above a predetermined threshold.

Channel selection 222 is a by-product of the heart rate estimation method. The channels are selected 222 based on the fusion of the cepstrum 206 as well as the compliance of heart rate estimation 214. A channel 224 is selected 222 at a moment of an analysis window, where its cepstral coefficient is taken as the highest value in the fused cepstrum and the particular cepstral coefficient is relevant to the estimated heart rate.

In accordance with the present embodiment, an experimental sensor matt having two rows of FBG sensors, each row having six sensors was provided on a mattress. One row was located at roughly an upper chest position of a subject lying on the mattress and the other row was located at roughly a lower chest position of the subject lying on the mattress. Twelve subjects participated in data collection, where the age, gender, height and weight of the subjects varied. Each subject laid on the mattress for a total of twenty minutes, with ten minutes in a flat posture and ten minutes in a sideways posture.

In order to verify the experimental results, electrocardiography (ECG) signals were simultaneously collected and the heart rate estimated in beats per minute (BPM) was compared with the ECG signals. An acceptance rate was also calculated as the percentage of time that a heart rate reading can be estimated from the BCG.

Figure 8:
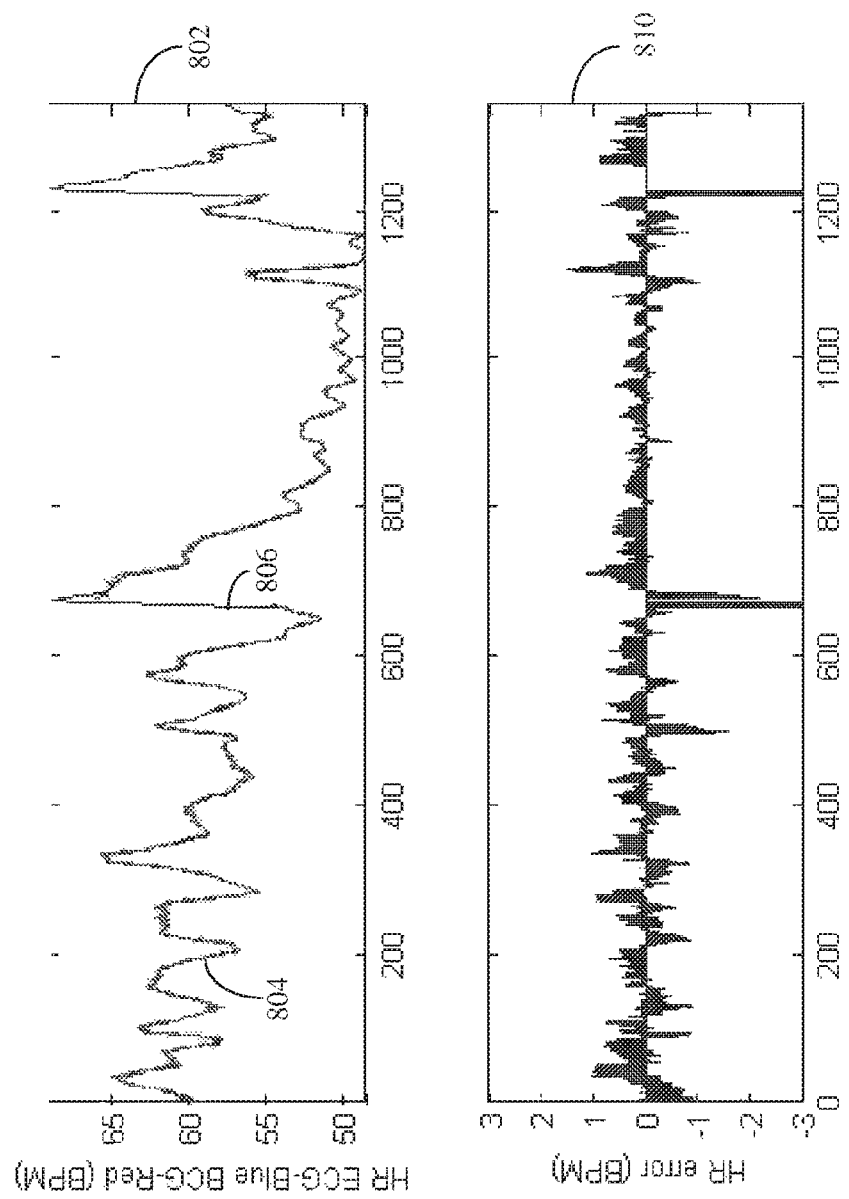
FIG. 8 depicts plots of experimental results of heart rate estimation from the BCG system of FIG. 1 determined in accordance with the present embodiment as compared with heart rate calculated from electrocardiography (ECG) signals as groundtruth from the same subjects.

Referring to FIG. 8, a plot 802 shows heart rate estimated from the BCG 804 and the reference heart rate from the ECG 806. A second plot 810 shows the heart rate error 812 between the BCG 804 and the ECG 806. The overall result of heart rate estimation of the twelve subjects is shown in a table 900 in FIG. 9 and the acceptance rate of the BCG estimation in accordance with the present embodiment is shown in a table 1000 in FIG. 10.

Figure 11:
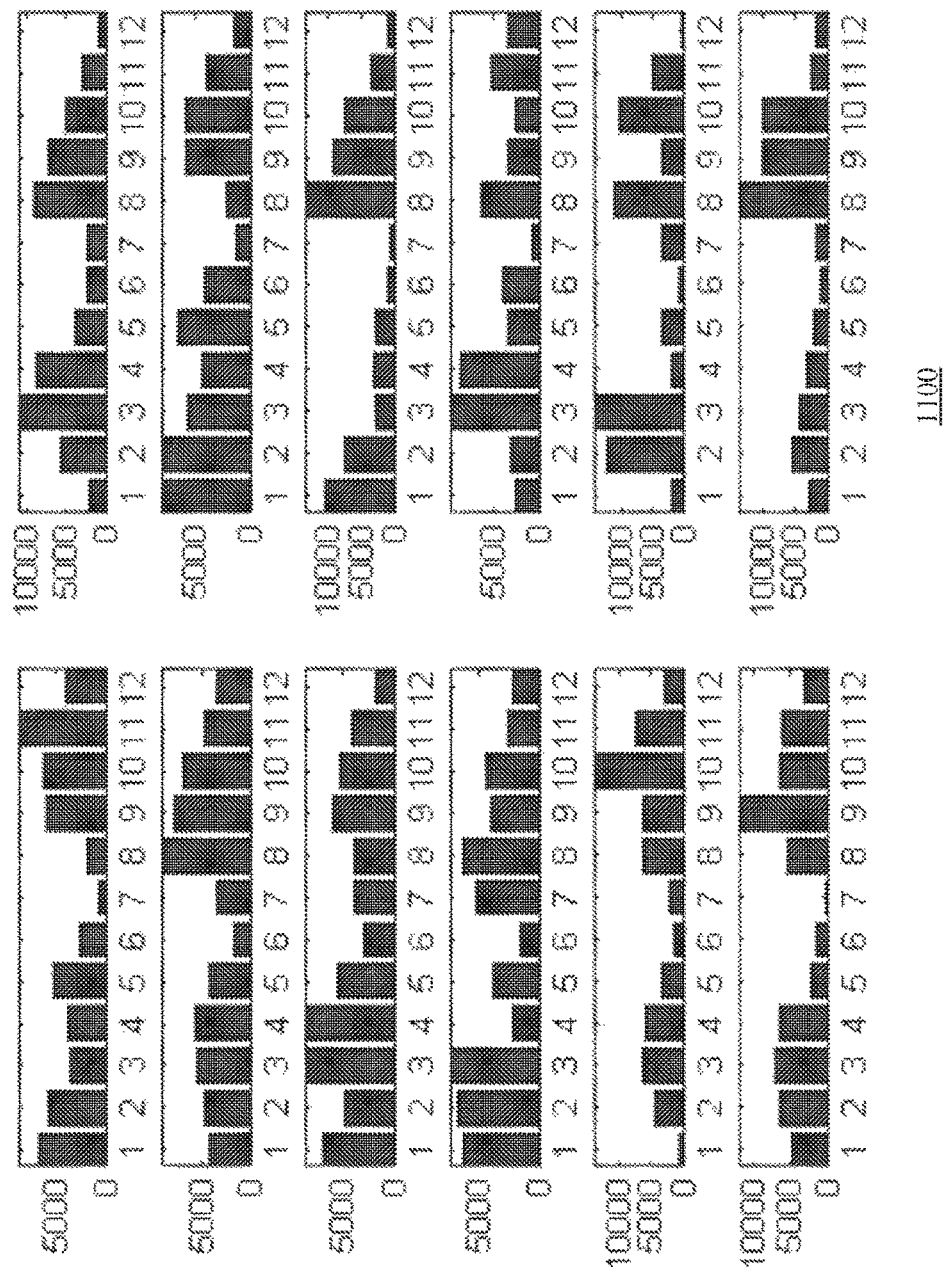
FIG. 11 depicts histograms of the experimental results of FIG. 9 showing channel selection results in accordance with the present embodiment.

Referring to FIG. 11, an illustration 1100 of twelve histograms depicts the channel selection of the twelve subjects. For each subject, a histogram of twelve bins shows the time where each sensor out of the twelve FBG sensors was selected. It is quite apparent that sensors located closer to the middle area of the mattress have a higher chance of being selected for most subjects.

Thus, it can be seen that the present embodiment provides a multichannel BCG analysis method based on a novel smoothed cepstrum calculation to represent the signal in cepstral domain. Using this representation, multiple channels can advantageously be fused for higher reliability and sensitivity of heart rate estimation. The selected channels with high quality levels can be used in further heart rate analysis such as finer level inter-beat interval estimation and heart rate variability calculations.

While exemplary embodiments have been presented in the foregoing detailed description of the invention, it should be appreciated that a vast number of variations exist.

It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of elements and method of operation described in an exemplary embodiment without departing from the scope of the invention as set forth in the appended claims.

What is claimed is:

1. A method for ballistocardiography comprising:
    digitizing a plurality of signals received from a corresponding plurality of sensors;
    estimating a plurality of smoothed cepstra corresponding to each of the plurality of digitized signals in response to a smoothed cepstrum analysis of a digital signal at a reception time of each of the plurality of digitized signals;
    estimating a fused cepstrum for the plurality of digitized signals in response to the plurality of smoothed cepstra; and
    determining a heart rate in response to the plurality of smoothed cepstra and the fused cepstrum.

2. The method in accordance with claim 1 wherein the estimating the plurality of cepstra comprises for each of the plurality of digitized signals:
    sampling the digitized signal in a plurality of time shifted predefined time windows to obtain a plurality of time domain samples;
    estimating a power spectrum of the plurality of time domain samples by logarithmic smoothing a discrete Fourier transform of the plurality of time domain samples; and
    estimating the smoothed cepstrum corresponding to the digitized signal by applying a frequency domain window function to the estimated power spectrum before inverse Fourier transforming the windowed estimated power spectrum of the plurality of time domain samples.

3. The method in accordance with claim 1 wherein the estimating the fused cepstrum comprises selecting a highest value of each of the plurality of smoothed cepstra at each lag time index of the plurality of digitized signals.

4. The method in accordance with claim 1 wherein the determining the heart rate step comprises detecting cepstral peaks within each of the plurality of cepstra and the fused cepstrum.

5. The method in accordance with claim 4 wherein the detecting cepstral peaks step comprises
    detecting a highest value within a predetermined time range for each of the plurality of smoothed cepstra.

6. The method in accordance with claim 4 wherein the determining the heart rate step further comprises
    determining the heart rate in response to a plurality of average heart rates, the plurality of average heart rates calculated for each of the plurality of cepstra and for the fused cepstrum.

7. The method in accordance with claim 6 wherein the calculating the plurality of average heart rates comprises for each of the plurality of smoothed cepstra:
    determining a percentage of the smoothed cepstrum comprising the detected cepstral peaks;
    if the percentage is determined to be greater than or equal to a predetermined percentage of the smoothed cepstrum, calculating the average heart rate by a mean time of a difference between an end of one of the detected cepstral peaks and a start of a next one of the detected cepstral peaks; and
    if the percentage is determined to be less than a predetermined percentage of the smoothed cepstrum, setting the average heart rate equal to null.

8. The method in accordance with claim 6 wherein the determining the heart rate comprises determining whether the average heart rate of the fused cepstrum is within a predefined error margin of the average heart rates of greater than a predetermined number of each of the plurality of cepstra.

9. The method in accordance with claim 8 further comprising the
    dynamically selecting one of the plurality of digitized signals received from the corresponding plurality of sensors for monitoring heart beats in response to the average heart rate of one of the plurality of cepstra corresponding to the one of the plurality of digitized signals having a highest value average heart beat that corresponds to the average heart rate of the fused cepstrum.

10. A ballistocardiography (BCG) system for heart beat determination comprising:
    a plurality of BCG sensors for generating a corresponding plurality of BCG signals in response to a subject's movement at a location of each of the plurality of BCG sensors;
    a BCG analyzer for determining a heart rate of the subject in response to the plurality of BCG signals; and
    a plurality of communication channels coupled to each of the plurality of BCG sensors and the BCG analyzer for providing the plurality of BCG signals from each of the plurality of BCG sensors to the BCG analyzer, wherein the BCG analyzer is configured to determine the heart rate of the subject by:
    digitizing the plurality of BCG signals;
    estimating a plurality of smoothed cepstra corresponding to each of the plurality of digitized BCG signals in response to a smoothed cepstrum analysis of a digital signal magnitude at a reception time of each of the plurality of digitized BCG signals;
    estimating a fused cepstrum for the plurality of digitized BCG signals in response to the plurality of smoothed cepstra; and
    determining the heart rate of the subject in response to the plurality of smoothed cepstra and the fused cepstrum.

11. The BCG system in accordance with claim 10 wherein the step of the BCG analyzer estimates the plurality of cepstra by for each of the plurality of digitized signals:
    sampling the digitized signal in a plurality of time shifted predefined time windows to obtain a plurality of time domain samples;

estimating a power spectrum of the plurality of time domain samples by logarithmic smoothing a discrete Fourier transform of the plurality of time domain samples; and estimating the smoothed cepstrum corresponding to the digitized signal by applying a frequency domain window function to the estimated power spectrum before inverse Fourier transforming the windowed estimated power spectrum of the plurality of time domain samples.

12. The BCG system in accordance with claim 10 wherein the BCG analyzer estimates the fused cepstrum by selecting a highest value of each of the plurality of smoothed cepstra at each lag time index of the plurality of digitized signals.

13. The BCG system in accordance with claim 10 wherein the BCG analyzer determines the heart rate by detecting cepstral peaks within each of the plurality of cepstra and the fused cepstrum.

14. The BCG system in accordance with claim 13 wherein the BCG analyzer detects cepstral peaks by detecting a highest value within a predetermined time range for each of the plurality of smoothed cepstra.

15. The BCG system in accordance with claim 13 wherein the BCG analyzer further determines the heart rate in response to a plurality of average heart rates, the plurality of average heart rates calculated for each of the plurality of cepstra and for the fused cepstrum.

16. The BCG system in accordance with claim 15 wherein the BCG analyzer calculates the plurality of average heart rates for each of the plurality of smoothed cepstra by:

determining a percentage of the smoothed cepstrum comprising the detected cepstral peaks;

if the percentage is determined to be greater than or equal to a predetermined percentage of the smoothed cepstrum, calculating the average heart rate by a mean time of a difference between an end of one of the detected cepstral peaks and a start of a next one of the detected cepstral peaks; and if the percentage is determined to be less than a predetermined percentage of the smoothed cepstrum, setting the average heart rate equal to null.

17. The BCG system in accordance with claim 15 wherein the BCG analyzer further determines the heart rate by determining whether the average heart rate of the fused cepstrum is within a predefined error margin of the average heart rates of greater than a predetermined number of each of the plurality of cepstra.

18. The BCG system in accordance with claim 10 wherein the BCG analyzer further calculates quality rankings for each of the plurality of communication channels in response to the average heart rate of each of the plurality of cepstra corresponding to each of the plurality of communication channels, the BCG analyzer further dynamically selecting one of the plurality of communication channels for monitoring heart beats in response to the average heart rate of one of the plurality of cepstra corresponding to the quality ranking of the selected one of the plurality of communication channels indicating that it has a highest value average heart beat that corresponds to the average heart rate of the fused cepstrum.

19. The BCG system in accordance with claim 10 further comprising a bandpass filter coupled to each of the plurality of communication channels for passing to the BCG analyzer signals including frequencies corresponding to heart beat related information while rejecting signals including other frequencies.

20. The BCG system in accordance with claim 19 wherein the other frequencies include frequencies corresponding to unrelated movement including low frequency respiratory information.

21. The BCG system in accordance with claim 10 wherein the plurality of communication channels comprise a plurality of communication channels, each of the plurality of communication channels including a transmitter coupled to a corresponding one of the plurality of BCG sensors, and wherein the BCG analyzer includes a receiver coupled to the plurality of communication channels.

22. The BCG system in accordance with claim 10 wherein each of the plurality of BCG sensors comprise a seismic sensor.

23. The BCG system in accordance with claim 10 wherein each of the BCG sensors are embedded on a supporting material, the location of each of the BCG sensors on the supporting material being defined in accordance with a predefined spatial layout and the plurality of BCG sensors generating the corresponding plurality of BCG signals in response to the subject's movement the subject is supported on the supporting material.

24. The BCG system in accordance with claim 23 wherein the supporting material is a bed mattress.

* * * * *